(12) United States Patent
Lindee et al.

(10) Patent No.: US 6,997,089 B2
(45) Date of Patent: Feb. 14, 2006

(54) OPTICAL GRADING SYSTEM FOR SLICER APPARATUS

(75) Inventors: Scott A. Lindee, Mokena, IL (US); Thomas C. Wolcott, La Grange, IL (US)

(73) Assignee: Formax, Inc., Mokena, IL (US)

( * ) Notice: Subject to any disclaimer, the term of this patent is extended or adjusted under 35 U.S.C. 154(b) by 0 days.

(21) Appl. No.: 10/179,549

(22) Filed: Jun. 25, 2002

(65) Prior Publication Data

US 2003/0233918 A1 Dec. 25, 2003

(51) Int. Cl.
*B26D 7/06* (2006.01)
*G01N 21/00* (2006.01)

(52) U.S. Cl. .............................. 83/29; 83/73; 83/76.8; 83/107; 83/520; 83/932

(58) Field of Classification Search ................. 83/932, 83/29, 23, 77, 107, 155, 76.8, 73, 520
See application file for complete search history.

(56) References Cited

U.S. PATENT DOCUMENTS

| | | | |
|---|---|---|---|
| 2,954,811 A | 10/1960 | Hensgen et al. | |
| 4,136,504 A | 1/1979 | Wyslotsky | |
| 4,226,540 A | 10/1980 | Barten et al. | |
| 4,413,279 A | 11/1983 | Gorl | |
| 4,557,019 A | 12/1985 | Van Devanter et al. | |
| 4,776,023 A | 10/1988 | Hamada et al. | |
| 4,875,254 A | 10/1989 | Rudy et al. | |
| 5,054,345 A | 10/1991 | Weber | |
| 5,136,906 A | 8/1992 | Antonissen et al. | |
| 5,267,168 A | 11/1993 | Antonissen et al. | |
| 5,499,719 A | 3/1996 | Lindee et al. | |

FOREIGN PATENT DOCUMENTS

| | | |
|---|---|---|
| DE | 41 13392 A1 | 10/1992 |
| DE | 199 15 861 A1 | 12/2000 |
| EP | 0 288 592 A1 | 1/1988 |
| EP | 0 500 478 | 8/1992 |
| GB | 1 507 683 | 4/1978 |
| GB | 2 187 281 | 9/1987 |
| GB | 2 285 126 | 6/1995 |
| WO | WO 95/21375 | 8/1995 |
| WO | WO 00-61338 | 10/2000 |

*Primary Examiner*—Charles Goodman
(74) *Attorney, Agent, or Firm*—The Law Office of Randall T. Erickson, P.C.

(57) ABSTRACT

A method of classifying slices or a portion cut from a food product according to an optical image of the slice. After a slice is removed from a food product loaf the slice is passed into an image field of a digital image receiving device. A control generates a pixel-by-pixel image data of the slice using input from the digital image receiving device. The control calculates a surface area of the slice from the data, and a fat content of the slice on a pixel-by-pixel basis. The fat content data is compared to at least one predetermined limit and the slice is classified accordingly.

14 Claims, 2 Drawing Sheets

OPTICAL GRADING SYSTEM FOR SLICER APPARATUS

TECHNICAL FIELD OF THE INVENTION

The present invention relates to slicing apparatus and associated conveyor and classifier systems for slicing and grouping food products. Particularly, the invention is directed to a food quality scanning and control system.

BACKGROUND OF THE INVENTION

Meat loaves are commonly sliced and the slices collected in groups in accordance with a particular weight requirement, the groups being packaged and sold at retail. The number of slices in a group may vary depending on the size and consistency of the meat loaf. For some products, neatly aligned stacked sliced groups are preferred, while for other products the groups are shingled so that a purchaser can see a part of every slice through transparent packaging.

Typically, round cross-section or square-section meat loaves are sliced into thin slices which are stacked or shingled in groups to be packaged and sold. These slices are then used by the consumer as cold cuts for sandwiches, and the like.

Slicing apparatus are disclosed, for example, in U.S. Pat. Nos. 5,649,463; 5,704,265; EP 0 713 753; or WO 99/08844, all herein incorporated by reference. Slicing apparatus and conveyor systems are also embodied in the FORMAX FX180 Slicer and FORMAX SNS Slicer available from Formax, Inc. of Mokena, Ill., U.S.A.

Meat carcasses can also be sliced into single slices or steaks for packaging or sliced in straight or shingled stacks as described above.

It is important when slicing and packaging meat products that quality of the meat being sliced and thereafter packaged is monitored. In this regard, it may be desirable that meat slices from the loaf or carcass of a predetermined grade have a predetermined maximum fat-to-lean ratio, and minimum amount of flaws, such as fat deposits, glands, isolated bits or voids.

U.S. Pat. Nos. 4,136,504; 4,226,540 and 4,413,279 disclose slice scanning systems wherein the cut slice of a food product is optically scanned for fat content and the resultant slice can be characterized accordingly.

The present inventors have recognized that it would be desirable to provide a system which would be directly responsive to the quality of cut slices and which would provide a compact and effective arrangement to classify slices based on fat content and fat deposits.

SUMMARY OF THE INVENTION

The invention provides a food slicing, conveying and classifying apparatus that determines the slice quality with regard to fat deposits, and can control the disposition of the scanned slice, or group of slices. The slices that have a greater than predetermined quantity of fat or flaws, can be classified as a rejected product, or an off-grade product to be sold at a reduced price.

The invention provides a method of classifying slices or portions cut from a food product, comprising the steps of:
removing a slice from a food product by cutting;
passing the slice into an image field of a digital image receiving device;
generating pixel-by-pixel image data of the slice using the digital image receiving device;
determining a surface area of the slice from the data;
determining a fat content of said slice on a pixel-by-pixel basis;
comparing the fat content to at least one predetermined limit; and
classifying the slice according to said limits.

The invention provides a system for classifying slices from a slicing machine based on fat content, comprising:
a slicing apparatus;
a conveyor arranged to receive slices from the slicing apparatus;
a control having a memory section and a data processing section;
an image capturing device arranged above the conveyor, the image capturing device signal-connected to the control to input into the memory section a two-dimensional pixel field corresponding to an image captured of a surface area of the slice, each pixel classified by the control as either a fat or lean portion of the surface area, depending on image, the control data processing section adapted to sum fat pixels and compare said sum of fat pixels to a predetermined limit; and
a classifying conveyor signal-connected to said control, the classifying conveyor movable to direct the slice to a destination depending on the number of fat pixels.

According to the invention, a slicing apparatus cuts and deposits a slice from a cut face of a food product loaf, onto a conveyor. The conveyor passes the slice beneath an image processing system. The image processing system includes a control or processor and an image capturing device such as a CCD type digital camera. The device is directed to scan a face of the slice. The device will capture an image of the slice, and the system will determine the slice outline or boundary and calculate the surface area. The system will determine and quantify the fat areas pixel-by-pixel that fall within the boundary of the slice. Any local fat pockets or deposits can be measured and quantified. Generalized or diffuse fat can also be quantified by a pixel-by-pixel analysis of the image.

Advantageously, the apparatus can include a weigh conveyor for weighing each slice or group of slices, and the image capturing device can be located above the weigh conveyor.

In response to the optical scanning of the slice, a conveyor classifier system can be activated to direct the scanned slice to an acceptable slice destination, a reject destination, or a grade-off destination.

Advantageously, in the production of straight stacks or shingled stacks of sliced product, each slice need not the scanned, rather, the top of each stack can be scanned to determine a fat-to-lean ratio, and the presence of flaws, after the stack has been cut and stacked from the loaf. The condition of the top slice, being cut from the loaf in the close vicinity of the remaining slices in the stack, is an accurate representation of the condition of all the slices in the stack.

It should be noted that the top slice of one stack is almost an exact representation of the bottom slice of the following stack. It may be advantageous to remember this image of the top slice of a stack and 'flag' it as also representing the bottom of the next stack to pass below the camera. Combined with the next following image, the actual top of the stack, it can be accurately estimated, by evaluating the bottom arid top slices of the stack, whether the entire stack meets the quality criteria. According to this procedure, it is not necessary to image each and every slice in the stack or draft to accurately characterize the quality of the stack.

Numerous other advantages and features of the present invention will be become readily apparent from the following detailed description of the invention and the embodiments thereof, from the claims and from the accompanying drawings.

DETAILED DESCRIPTION OF THE PREFERRED EMBODIMENTS

Figure 1:
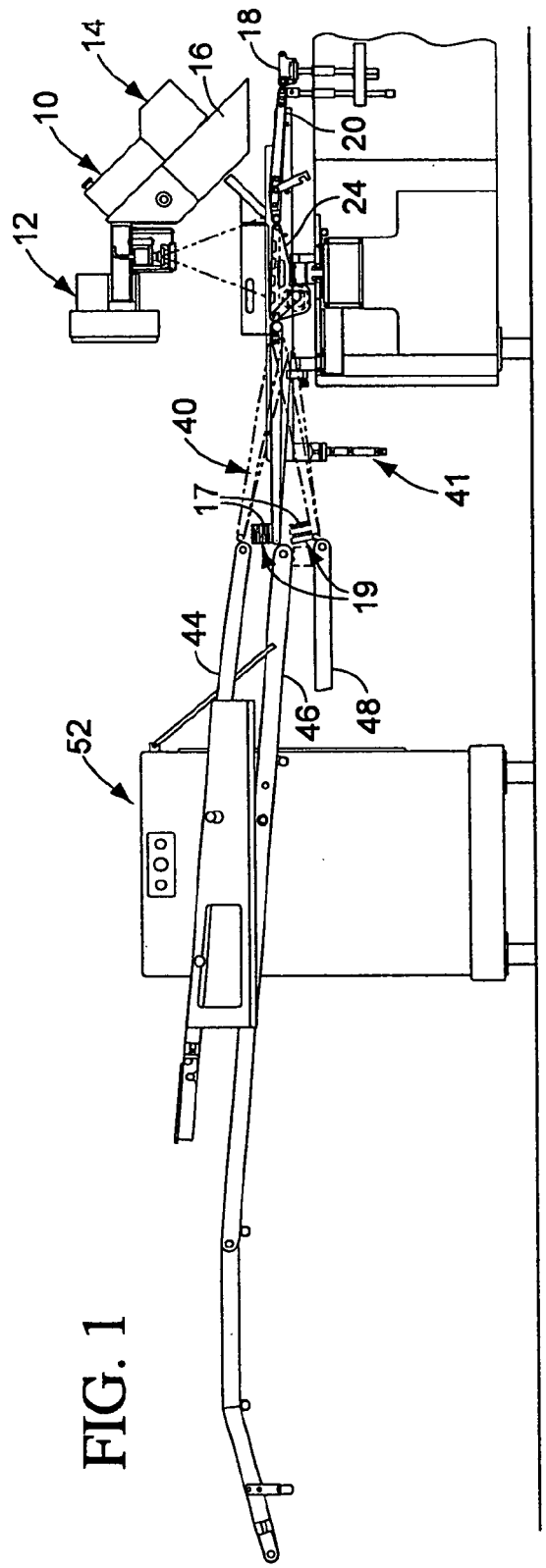
FIG. 1 is a diagrammatic, elevational view of a slicing, conveying and classifying apparatus of the present invention.

While this invention is susceptible of embodiment in many different forms, there are shown in the drawings, and will be described herein in detail, specific embodiments thereof with the understanding that the present disclosure is to be considered as an exemplification of the principles of the invention and is not intended to limit the invention to the specific embodiments illustrated.

FIG. 1 illustrates a versatile high-speed food loaf-slicing apparatus 10. Such a machine is generally disclosed, for example, in U.S. Pat. Nos. 5,704,265; 5,649,463; or in EP 0 713 753 A2; or WO 99/08844, all herein incorporated by reference.

The apparatus 10 can be controlled by a machine control or CPU (central processing unit) 12. The apparatus includes a slicing station 14 including a slicing head 16 having a blade (not shown) for removing slices 17 from a food product loaf or carcass (not shown). The slices 17 are deposited on a receiving conveyor 18. The receiving conveyor 18, also known as a "jump conveyor", moves horizontally slowly to form a shingled stack of slices (not shown), or remains stationary to form a straight stack of slices 19, such as slices of bologna or ham. Alternately, the slices can be single slices 17a, shown in FIG. 2, such as steaks or bacon cut from a carcass.

When forming stacks of slices, the receiving conveyor 18 can also be raised up to begin a new stack and moved down vertically as a stack is formed to ensure a short drop for each slice from the slicing blade to the receiving conveyor or to the preceding slice. Once the stack is formed, the receiving conveyor moves slices to a decelerating conveyor 20 which moves slices onto a weigh conveyor 24.

The weigh conveyor 24 can be configured, and the associated software programmed, as disclosed in PCT US01/40474, filed Apr. 9, 2001, herein incorporated by reference. The weigh conveyor determines slice or stack weight and communicates a weight signal to the CPU 12.

An image processing system 30 is arranged above the weigh conveyor 24. The system 30 includes an image capturing device such as a digital camera 34. The camera is preferably a digital CCD type camera.

The image processing system 30 can be controlled by the machine CPU 12, or can be a stand-alone system having a dedicated processor, memory and software. The system 30 preferably includes the following components:

1. ELECTRIM EDC-1000N black and white 640×480 pixel digital camera 34 with a 4.8 mm lens;
2. Digital frame grabber PC-104 printed circuit board;
3. PC-104 CPU main processor board;
4. Light source to provide illumination of the product;
5. Shroud 36, shown in FIG. 3, surrounding the camera 34 to block ambient light; and
6. Yellow or neutral colored transfer belting 37, shown in FIGS. 2 and 3, to provide a background contrast against the slice being viewed.

The digital frame grabber PC-104 printed circuit board and the PC-104 CPU main processor board can be located in the system 30 or in the CPU 12.

The transfer belting 37 of the weigh conveyor 24 delivers slices to a classifier conveyor 40 that is selectively pivoted by an actuator 41, by signal from the system 30 or from the CPU 12, to deliver slices alternately to a reject conveyor 44, a pass conveyor 46 and a grade-off conveyor 48. The actuator can be a pneumatic cylinder with an extendable/retractable rod 42 connected to the classifier conveyor 40, shown in FIG. 3. A make-weight station 52 can be located adjacent to the conveyor 44, 46, 48. A classifier conveyor system is described in U.S. Pat. No. 5,499,719 and is herein incorporated by reference.

Figure 2:
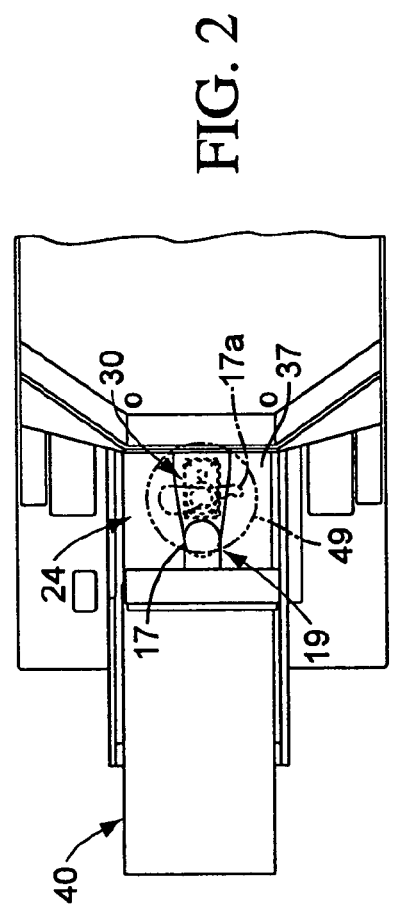
FIG. 2 is an enlarged, diagrammatic fragmentary plan view of the apparatus of FIG. 1.
Figure 3:
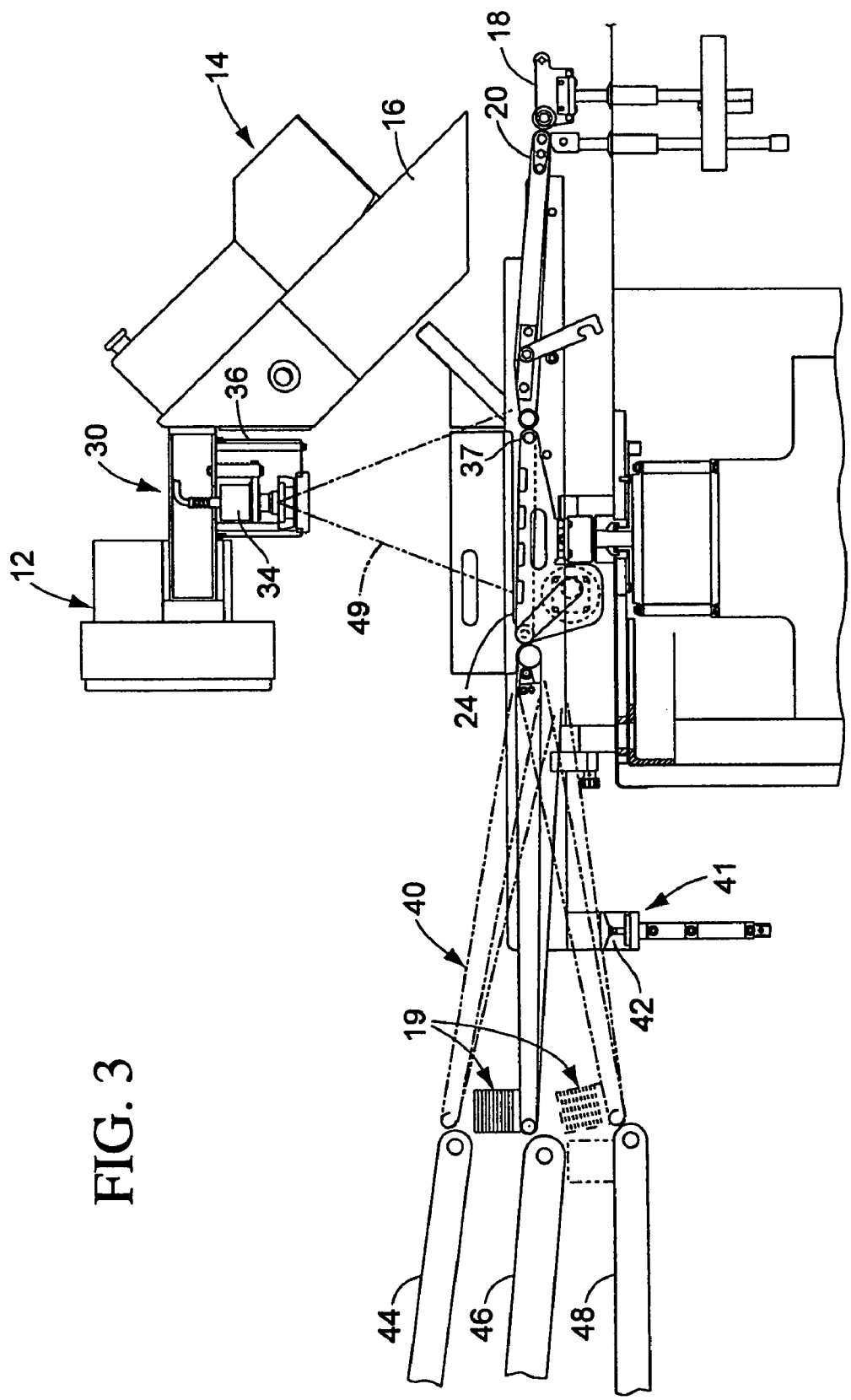
FIG. 3 is a diagrammatic, fragmentary elevational view of the apparatus of FIG. 2.

FIGS. 2 and 3 illustrate the image processing system 30 which captures the image of the slice passing on the scale 24. When the slicer weigh scale 24 senses the slice to be viewed on the scale, the CPU 12 triggers the system 30 to capture the slice image. The system 30 will capture an image of the top of the slice 17 on top of the stack 19 or, in the case of a single slice, the top of the slice 17a. The camera 34 captures the slice image within an image field of vision 49 pixel-by-pixel. The shutter speed of the camera is fast enough to capture the image while the slice or stack is in motion. The image is then retrieved from the digital frame grabber printed circuit board into the memory of the system 30 or of the CPU 12.

Software in the system 30 or in the CPU 12 can then perform various analyses on the digital image data. The slice perimeter or boundary dimensions are determined due to the brightness or color contrast between the slice and the weigh scale belting on which the slice is transferred. A grayscale analysis, pixel-by-pixel, can be undertaken by the software, wherein black is 0 and white is 255. An experimentally determined grayscale cutoff point between fat pixels (light) and lean pixels (dark) can be used to characterize each pixel as being fat or lean. The ratio of light pixels (fat) to dark pixels (lean) within the slice boundary is then calculated, as representative of a fat-to-lean ratio. Additionally, local areas constituting "flaws" in the slice can be quantified in size, by calculating and summing adjacent non-lean pixels, and then compared to a flaw tolerance or limit. A flaw can be a fat deposit, a gland, muscle or bone piece, a void, or other undesirable bit.

Alternatively, the calculations and routines utilized to capture and evaluate slice image data can be as described in U.S. Pat. Nos. 4,136,504; 4,226,540 and/or 4,413,279, all herein incorporated by reference. The mathematical analysis of pixel data can be as described in U.S. Pat. No. 5,267,168, herein incorporated by reference.

The data is calculated and compared to predetermined standards or customer programmable standards regarding overall fat content and flaw size and/or quantity limits.

A calculation is made to determine whether the slice is to be classified as a "pass", that is, being below stringent fat content or flaw limits, or "reject", that is being above acceptable fat content or flaw limits, or "grade-off", that is being below acceptable fat content or flaw limits but above stringent fat content or flaw limits.

Based on the calculated parameters and the comparison to the pre-selected tolerances, the slice is determined to be a grade reject if the fat-to-lean ratio is greater than the allowable tolerance, or if the slice includes a flaw, or a pre-selected number of flaws, greater in size, individually and/or in the aggregate, than an allowable tolerance. These tolerances can be adjustable and determined by the user, typically as a plant standard.

Advantageously, in the production of straight stacks or shingled stacks of sliced product, each slice need not the scanned, rather, the top of each stack can be scanned to determine a fat-to-lean ratio, and the presence of flaws, after the stack has been cut and stacked from the loaf. The condition of the top slice, being cut from the loaf in the close vicinity of the remaining slices in the stack, is an accurate representation of the condition of all the slices in the stack.

When grading stacks of slices, the top slice of one stack is almost an exact representation of the bottom slice of the following stack. It may be advantageous to remember this image of the top slice of a stack and 'flag' it as also representing the bottom of the next stack to pass below the camera. Combined with the next following image, the actual top of the stack, it can be accurately estimated, by evaluating the bottom and top slices of the stack, whether the entire stack meets the quality criteria. According to this procedure, it is not necessary to image each and every slice in the stack or draft to accurately characterize the quality of the stack.

Thus, the stack can then be characterized as a grade reject, grade off or acceptable stack based on the characteristics of one slice of the stack or based on the characteristics of the top and bottom slices of the stack.

If the slice or stack of slices is determined to be a grade reject, the classifier conveyor 40 will be pivoted by the actuator 41, by signal from the system 30 or the CPU 12 to place the slice or stack of slices on the reject conveyor belt 44. Acceptable product can be classified by the system into premium (pass) or economy (grade-off) grades and directed by the classifier conveyor 40, pivoted by the actuator 41, by signal from the system 30 or the CPU 12, onto the separate conveyor belts 46, 48, respectively. All out-of-weight tolerance slices or groups of slices, regardless of their visual acceptance, can be placed on the reject conveyor belt 44.

From the foregoing, it will be observed that numerous variations and modifications may be effected without departing from the spirit and scope of the invention. It is to be understood that no limitation with respect to the specific apparatus illustrated herein is intended or should be inferred. It is, of course, intended to cover by the appended claims all such modifications as fall within the scope of the claims.

The invention claimed is:

1. A method of classifying groups of slices collected in a stack after being cut from a food product, comprising the steps of:
   removing a plurality of slices in succession from a food product by cutting, using a high speed slicing apparatus;
   dropping said plurality of slices from said food product and accumulating said plurality into a stack on a conveyor system having at least one conveying surface;
   moving said stack on said conveying surface into an image field of a digital image receiving device;
   generating pixel-by-pixel image data of a top slice of said stack using the digital image receiving device;
   determining a surface area of the pot slice from the data;
   determining a fat content of said top slice on a pixel-by-pixel basis;
   comparing the fat content to at least one predetermined limit; and
   classifying said stack according to said fat content and said limit; and
   depending on how said stack is classified, conveying said stack to a corresponding destination.

2. The method according to claim 1, comprising the further step of weighing the stack at the same time as the step of generating pixel-by-pixel image data.

3. The method according to claim 1, wherein said step of classifying is further defined in that a classifying conveyor, a pass conveyor and a reject conveyor are provided, and said classifying conveyor is adjustable to direct the stack alternatively to said pass conveyor or said reject conveyor to transport said stack to said corresponding destination.

4. The method according to claim 1, comprising the further step of determining the size of any fat deposits within said top slice by adding adjacent pixels of fat materials.

5. The method according to claim 1, wherein said step of classifying is further defined in that a classifying conveyor, a pass conveyor, a grade off conveyor and a reject conveyor are provided, and said classifying conveyor is adjustable to direct the stack alternatively to said pass conveyor, said grade off conveyor or said reject conveyor.

6. The method according to claim 1, comprising the further step of weighing the stack at the same time as the step of generating pixel-by-pixel image data; and wherein said step of classifying is further defined in that a classifying conveyor, a pass conveyor and a reject conveyor are provided, and said classifying conveyor is adjustable to direct the stack alternatively to said pass conveyor or said reject conveyor; and comprising the further step of determining the size of any fat deposits within said top slice by adding adjacent pixels of fat materials.

7. The method according to claim 6 wherein said stack is classified according to the classification of a top slice of a preceding stack and said top slice of said stack.

8. The method according to claim 1 wherein said stack is classified according to the classification of a top slice of a preceding stack and said top slice of said stack.

9. A system for classifying slices from a slicing machine based on fat content, comprising:
   a high speed slicing apparatus arranged to cut off a series of slices from a food loaf;
   a conveyor arranged to receive said slices from said slicing apparatus in a stack of slices;
   a control having a memory section and a data processing section;
   an image capturing device arranged above the conveyor, said image capturing device signal-connected to said control to input into said memory section a two-dimensional pixel field corresponding to an image captured of a surface area of a top slice of said stack of slices located on said conveyor, each pixel classified by said control as either a fat or lean portion of the surface area, depending on image, said control data processing section adapted to sum fat pixels and compare said sum of fat pixels to a predetermined limit; and
   a classifying conveyor signal-connected to said control, said classifying conveyor movable to direct the stack of slices to a destination depending on the number of fat pixels.

10. The system according to claim 9, wherein said image capturing device comprises a digital camera.

11. The system according to claim 9, wherein said conveyor comprises a weigh conveyor, and said camera is located above said weigh conveyor and is directed downward on said stack located on said weigh conveyor.

12. The system according to claim 9, wherein said image capturing device comprises a digital camera; and wherein said conveyor comprises a weigh conveyor, and said camera is located above said weigh conveyor and directed downward on said stack located on said weigh conveyor.

13. A method of classifying stacks of slices cut from a food product, comprising the steps of:
removing a plurality of slices from a food product by cutting said food product using a high speed slicing apparatus and collecting said slices in a current stack;
passing a slice that represents a top slice of said current stack into an image field of a digital image receiving device;
generating pixel-by-pixel image data of the top slice using the digital image receiving device;
determining a surface area of the top slice from the data;
determining a fat content of said top slice on a pixel-by-pixel basis;
comparing the fat content to at least two predetermined limits that define pass, grade off and reject classifications; and
classifying the current stack according to said fat content and said limits; and
conveying said pass, said grade off and said reject classified stacks to corresponding destinations.

14. The method according to claim 13 wherein said current stack is classified according to the classification of a top slice of a preceding stack and said top slice of said current stack.

* * * * *

UNITED STATES PATENT AND TRADEMARK OFFICE
CERTIFICATE OF CORRECTION

PATENT NO. : 6,997,089 B2 Page 1 of 1
APPLICATION NO. : 10/179,549
DATED : February 14, 2006
INVENTOR(S) : Scott A. Lindee and Thomas C. Wolcott It is certified that error appears in the above-identified patent and that said Letters Patent is hereby corrected as shown below:

At column 2, line 62, change "arid" to --and--.

At column 5, line 61, change "pot" to --top--.

Signed and Sealed this

Twenty-ninth Day of August, 2006

JON W. DUDAS
*Director of the United States Patent and Trademark Office*

(12) INTER PARTES REVIEW CERTIFICATE (3207th)

United States Patent
Lindee et al.

(10) Number: US 6,997,089 K1
(45) Certificate Issued: Aug. 4, 2023

(54) OPTICAL GRADING SYSTEM FOR SLICER APPARATUS

(75) Inventors: Scott A. Lindee; Thomas C. Wolcott

(73) Assignee: PROVISUR TECHNOLOGIES, INC.

Trial Number:

IPR2019-01466 filed Aug. 9, 2019

Inter Partes Review Certificate for:

Patent No.: 6,997,089
Issued: Feb. 14, 2006
Appl. No.: 10/179,549
Filed: Jun. 25, 2002

The results of IPR2019-01466 are reflected in this inter partes review certificate under 35 U.S.C. 318(b).

INTER PARTES REVIEW CERTIFICATE
U.S. Patent 6,997,089 K1
Trial No. IPR2019-01466
Certificate Issued Aug. 4, 2023

AS A RESULT OF THE INTER PARTES REVIEW PROCEEDING, IT HAS BEEN DETERMINED THAT:

Claims 1-14 are cancelled.

\* \* \* \* \*